United States Patent [19]

Oka et al.

[11] 4,199,582

[45] Apr. 22, 1980

[54] PIPERAZINE CONTAINING DIHYDRONAPHTHALENE DERIVATIVES AND COMPOSITIONS

[75] Inventors: Yoshikazu Oka, Kobe; Katsumi Itoh; Minoru Hirata, both of Takatsuki, all of Japan

[73] Assignee: Takeda Chemical Industries, Ltd., Osaka, Japan

[21] Appl. No.: 928,156

[22] Filed: Jul. 26, 1978

[30] Foreign Application Priority Data

Aug. 2, 1977 [JP] Japan .................................. 52/93089

[51] Int. Cl.² ................ C07D 295/12; A61K 31/495; A61K 31/535
[52] U.S. Cl. ................................ 424/250; 424/248.4; 260/243.3; 544/120; 544/360; 544/372; 544/396
[58] Field of Search ............................. 544/360, 372; 260/243.3; 424/250

[56] References Cited

FOREIGN PATENT DOCUMENTS 49-11713  3/1974  Japan ........................ 544/460

Primary Examiner—John M. Ford
Assistant Examiner—R. W. Ramsuer
Attorney, Agent, or Firm—Wenderoth, Lind & Ponack

[57] ABSTRACT

Novel 1,2-dihydronaphthalene derivatives of the formula

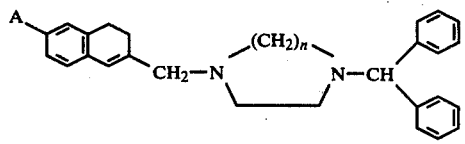

wherein A is a di-lower alkylamino group or a 5- to 7-membered cyclic amino group which may contain one oxygen atom and n is 2 or 3, and its salts have excellent pharmacological activities such as vasodilator, hypotensive and cerebral blood flow increasing actions.

5 Claims, No Drawings

PIPERAZINE CONTAINING DIHYDRONAPHTHALENE DERIVATIVES AND COMPOSITIONS

The present invention relates to novel and useful 1,2-dihydronaphthalene derivatives.

The present inventors have succeeded in producing novel 1,2-dihydronaphthalene derivatives of the formula

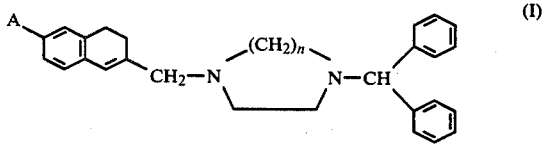

wherein A is a di-lower alkylamino group or a 5- to 7-membered cyclic amino group which may contain one oxygen atom and n is 2 or 3, and its acid addition salt, and further studies on these compounds have unexpectedly revealed that they exhibit excellent pharmacological activities such as vasodilator, hypotensive and cerebral blood flow increasing actions, and are of value, for example, as antihypertensives, as drugs for the management of impaired cerebral circulation and as peripheral vasodilators.

Thus, the principal object of the present invention is to provide the novel 1,2-dihydronaphthalene derivatives (I) and their acid addition salts which have the excellent pharmacological activities, and another object is to provide a pharmaceutical composition comprising one or more of these compounds. A further object is to provide an industrially feasible method for producing these compounds. Other objects will be made clear from the description and claims presented hereinafter.

Referring to the formula (I), the di-lower alkylamino group designated by A is an amino group which is disubstituted preferably by lower alkyls from 1 to 4 carbon atoms, such as dimethylamino, diethylamino, dipropylamino, dibutylamino and so on. Particularly preferred are dimethylamino and diethylamino. The 5- to 7-membered cyclic amino group, also designated by A, may include one oxygen atom in its cyclic structure, being exemplified by 1-pyrrolidinyl, piperidino, homopiperidinyl, morpholino and so on.

The 1,2-dihydronaphthalene derivatives of the formula (I) and salts thereof may be produced in good yield, for example, by subjecting a compound of the formula

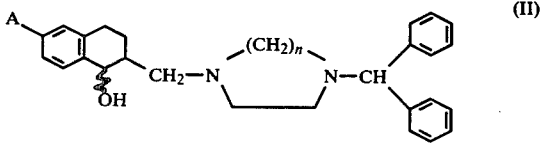

wherein A and n have the same meanings as defined above to dehydration reaction. This dehydration reaction is generally accomplished by placing a compound (II) under conditions of dehydration in an appropriate solvent. While the conditions of dehydration may be established by any technique per se known to one skilled in organic chemistry, preferred techniques include the following. Thus, by way of example, one may conduct the reaction by the presence of a mineral acid, e.g. hydrochloric acid, sulfuric acid or nitric acid; a Lewis acid, e.g. aluminum chloride, zinc chloride and boron trifluoride; a phosphoric acid compound, e.g. phosphoric acid and polyphosphoric acid; an organic acid, e.g. acetic acid, propionic acid, benzenesulfonic acid, p-toluenesulfonic acid and methanesulfonic acid; or an acid salt such as sodium hydrogen sulfate and potassium hydrogen sulfate. An alternative procedure comprises reacting the starting compound with a dehydrating agent such as an acid anhydride, e.g. acetic anhydride, propionic anhydride, phthalic anhydride or phosphoric anhydride, or an acid halide, e.g. phosphorus oxychloride or thionyl chloride. The solvent may be any one that will not interfere with the reaction. Thus, for example, water, methanol, ethanol, isopropanol, acetone, methyl ethyl ketone, ethyl acetate, chloroform, diethyl ether, benzene, toluene, dioxane, tetrahydrofuran, dimethylsulfoxide, dimethylformamide, pyridine and triethylamine as well as mixtures of such solvents may be mentioned. Depending upon the types of dehydrating agent, solvent and compound (II) employed, among other conditions, the reaction may normally be accomplished successfully at temperatures within the range of about 0° C. to about 200° C. In conducting this dehydration reaction, the starting compound (II) may be employed in the form of free base or as an acid addition salt similar to that which will hereinafter be mentioned in connection with the compounds (I).

The 1,2-dihydronaphthalene derivatives (I) thus produced may be isolated in the form of free base or as an acid addition salt, by conventional separation and purification procedures such as extraction, concentration, neutralization, filtration, recrystallization, distillation and column chromatography. By procedures known per se, the free base may be converted to physiologically acceptable acid addition salts such as inorganic acid salts (e.g. hydrochloride, hydrobromide, sulfate, nitrate) or organic acid salts (e.g. maleate, fumarate, malate, tartrate, toluenesulfonate, naphthalenesulfonate, methanesulfonate).

The novel 1,2-dihydronaphthalene derivatives of the formula (I) and salts thereof according to this invention have an excellent vasodilator action and are characterized by having excellent hypotensive as well as cerebral blood flow increasing actions based upon the said vasodilator action and also by their low toxicity. Thus, these compounds are of value as drugs, for example, for the treatment of circulatory failure such as hypertension and impaired cerebral circulation, and as peripheral vasodilators in mammalian animals (human beings; domesticated animals such as dogs and cats; laboratory animals such as rats and mice). Where the compound of this invention is employed as such a drug, it may be administered orally or parenterally either as it is or as formulated with suitable pharmaceutically acceptable carriers, excipients or diluents in such varied dosage forms as powders, granules, tablets, capsules and injections. The dosage may be chosen depending on the disease to be managed and the route of administration. For instance, when the present compounds are administered to adult humans as a drug for the treatment of the disturbance of cerebral circulation, e.g. for the treatment of cerebral apoplexy (cerebral haemorrhage, cerebral thrombosis and cerebral embolism), cerebral arteriosclerosis, hypertensive cerebral circulatory insufficiency, sequelae of head injury, etc., advantageous dose levels are of about 10 to 500 mg., especially about 20 to 200 mg. daily by the oral route, or about 1 to 50 mg., especially about 2 to 20 mg. daily by the intravenous route. When the present compounds are administered to human adults as a drug for the treatment of essential hypertension (hyperpiesia), the preferred dosage is about 20 to 200 mg. daily by the oral route.

The starting compound (II) employed in this invention may be easily produced, for example by the method described in "Archiv der Pharmazie" 275, 54 et seq. (1937) by a method similar thereto, by the following route of synthesis:

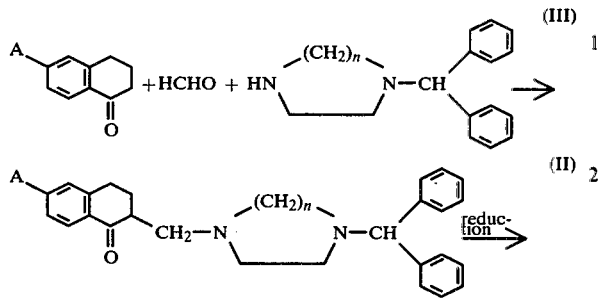

In the above formulas, A and n have the same meanings as defined hereinbefore.

The starting compound (II) has several isomers with respect to the asymmetric carbon atom and, normally, are obtained as a mixture of such isomers, although the compound (II) may be obtained stereospecifically in certain instances. The racemic mixture may be resolved, if desired, by the conventional method, e.g. by salt formation with an optically active acid or base. In this invention, both such an isomer of compound (II) and a racemic mixture of such isomers may be employed.

The starting compound (III) in the above reaction scheme may be easily produced, for example by the method described in U.S. Pat. No. 3,322,760 (1967) or a method similar thereto.

The following Examples and Experiments are further illustrative of this invention. It should, of course, be understood that the scope of the invention is by no means limited by and to these examples.

Throughout the foregoing description as well as in the following Examples and Experiments, "g.", "ml." and "°C." respectively refer to "gram(s)", "milligram(s)", "milliliter(s)" and "degree(s) centigrade".

EXAMPLE 1

In 50 ml. of ethanol was dissolved a mixture of 2 g. of 6-morpholino-3,4-dihydro-1(2H)-naphthalenone hydrochloride, 4 g. of 1-benzhydrylpiperazine hydrochloride and 4 g. of a 37% aqueous solution of formalin. The solution was allowed to stand at room temperature for 10 days, after which it was neutralized with an aqueous solution of sodium hydrogen carbonate and extracted with 100 ml. of chloroform. The extract was dried over anhydrous sodium sulfate and the solvent was distilled off under reduced pressure. By the above procedure there was obtained 5 g. of 2-[(4-benzhydryl-1-piperazinyl)methyl]-6-morpholino-3,4-dihydro-1(2H)-naphthalenone as colorless oil. IR$\nu_{c=o}$ $^{neat}$ 1665 cm$^{-1}$. This oil was dissolved in 50 ml. of methanol and stirred with 3 g. of sodium borohydride at room temperature for 30 minutes. The reaction mixture was diluted with 500 ml. of water and extracted with 150 ml. of chloroform. The extract was dried and distilled under reduced pressure to remove the solvent, whereupon 4.5 g. of 2-[(4-benzhydryl-1-piperazinyl)methyl]-6-morpholino-1,2,3,4-tetrahydro-1-naphthalenol was obtained as an oil. A portion of this oil was purified by chromatography on a column of silica gel and lead to its fumarate melting at 184°-187° C.(decomposition).

Elemental analysis: Calculated for $C_{32}H_{39}N_3O_2 \cdot C_4H_4O_4$: C, 70.45; H, 7.06; N, 6.85. Found: C, 70.22; H, 7.09; N, 6.88.

In 50 ml. of 20% ethanolic HCl was dissolved 4 g. of the above unpurified oil and the solution was heated under reflux for 2 hours. After cooling, the crystals produced were recovered by filtration. By the above procedure there was obtained 1.5 g. of 3-[(4-benzhydryl-1-piperazinyl)methyl]-7-morpholino-1,2-dihydronaphthalene hydrochloride as colorless prisms melting at 193°-197° C.(decomposition).

Elemental analysis: Calculated for $C_{32}H_{37}N_3O \cdot 3HCl \cdot H_2O$: C, 63.31; H, 6.97; N, 6.92. Found: C, 62.84; H, 6.67; N, 6.95.

EXAMPLE 2

In 100 ml. of ethanol was dissolved 2 g. of 6-dimethylamino-3,4-dihydro-1(2H)-naphthalenone hydrochloride, 4 g. of 1-benzhydrylpiperazine hydrochloride and 4 g. of a 37% aqueous solution of formalin and the reaction was carried out at room temperature for 2 hours. The reaction mixture was diluted with 500 ml. of water, neutralized with sodium hydrogen carbonate and extracted with chloroform. The chloroform extract was dried and distilled under reduced pressure to remove the solvent, whereupon 2-[(4-benzhydryl-1-piperazinyl)methyl]-6-dimethylamino-3,4-dihydro-1(2H)-naphthalenone was obtained as an oil. This oily product was dissolved in 50 ml. of methanol and stirred with 2.5 g. of sodium borohydride at room temperature for 30 minutes. The reaction mixture was diluted with 500 ml. of water and extracted with chloroform. The extract was dried and the solvent was distilled off under reduced pressure. By the above procedure there was obtained 2-[(4-benzhydryl-1-piperazinyl)methyl]-6-dimethylamino-1,2,3,4-tetrahydro-1-naphthalenol as an oil. This oil was dissolved in 50 ml. of ethanolic HCl and the solution was heated under reflux for 2 hours. Upon cooling there was obtained 1.5 g. of 3-[(4-benzhydryl-1-piperazinyl)methyl]-7-dimethylamino-1,2-dihydronaphthalene hydrochloride as colorless needles melting at 190°-195° C.(decomposition).

Elemental analysis: Calculated for $C_{30}H_{35}N_3 \cdot 3HCl \cdot \frac{1}{2}H_2O$: C, 64.80; H, 7.07; N, 7.56. Found: C, 64.80; H, 7.04; N, 7.83.

EXAMPLE 3

In 50 ml. of ethanol was dissolved a mixture of 2 g. of 6-piperidino-3,4-dihydro-1(2H)-naphthalenone hydrochloride, 4 g. of 1-benzhydrylpiperazine hydrochloride and 4 g. of a 37% aqueous solution of formalin. The solution was allowed to stand at room temperature for 10 days, after which it was neutralized with aqueous sodium hydrogen carbonate and extracted with chloroform. The extract was dried and the solvent was distilled off under reduced pressure, whereby 2-[(4-benzhydryl-1-piperazinyl)methyl]-6-piperidino-3,4-dihydro-1(2H)-naphthalenone was obtained as an oil. This oil was dissolved in 50 ml. of methanol and the solution was stirred with 3 g. of sodium borohydride at room temperature for 30 minutes. The reaction mixture was diluted with 500 ml. of water and extracted with chloroform. The extract was dried and the solvent was distilled off under reduced pressure. By the above procedure there was obtained 2-[(4-benzhydryl-1-piperazinyl)methyl]-6-piperidino-1,2,3,4-tetrahydro-1-naphthalenol as an oil. This oily product was dissolved in 50 ml. of 20% ethanolic HCl and the solution was heated under reflux for 2 hours. After cooling, the crystals were collected by filtration, whereby 2.7 g. of 3-[(4-benzhydryl-1-piperazinyl)methyl]-7-piperidino-1,2-dihydronaphthalene hydrochloride was obtained as colorless prisms melting at 195°–199° C.(decomposition).

Elemental analysis: Calculated for $C_{33}H_{39}N_3.3HCl.H_2O$: C, 65.50; H, 7.33; N, 6.95. Found: C, 65.38; H, 7.13; N, 7.23.

EXAMPLES 4–7

By procedures similar to those described in Examples 1 to 3, the following compounds were produced.

3-[(4-Benzhydryl-1-piperazinyl)methyl]-7-diethylamino-1,2-dihydronaphthalene hydrochloride, m.p.195°–220° C.(gradually decomposed).

Elemental analysis: Calculated for $C_{32}H_{39}N_3.3HCl.H_2O$: C, 64.80; H, 7.48; N, 7.09. Found: C, 64.81; H, 7.21; N, 6.96.

3-[(4-Benzhydryl-1-piperazinyl)methyl]-7-dibutylamino-1,2-dihydronaphthalene hydrochloride, m.p.175°–180° C.(decomposition)

Elemental analysis: Calculated for $C_{36}H_{47}N_3.3HCl$: C, 68.50; H, 7.98; N, 6.66. Found: C, 68.21; H, 8.17; N, 6.77.

3-[(4-Benzhydryl-1-piperazinyl)methyl]-7-(1-pyrrolidinyl)-1,2-dihydronaphthalene hydrochloride, m.p.185°–190° C. (decomposition)

Elemental analysis: Calculated for $C_{32}H_{37}N_3.3HCl.3/2H_2O$: C, 64.05; H, 7.22; N, 7.00. Found: C, 64.19; H, 6.96; N, 6.81.

3-[(4-Benzhydryl-1-piperazinyl)methyl]-7-(1-homopiperidinyl)-1,2-dihydronaphthalene hydrochloride, m.p.187°–190° C.(decomposition)

Elemental analysis:
Calculated for $C_{34}H_{41}N_3.3HCl.H_2O$: C, 65.96; H, 7.49; N, 6.79. Found: C, 65.59; H, 7.25; N, 6.39.

EXAMPLE 8

The reaction and treatment of Example 1 was repeated except that 1-benzhydrylhomopiperazine hydrochloride was used as the starting compound and that the reaction mixture, resulting from the refluxing with ethanolic hydrochloric acid in the last step, was diluted with ethyl acetate to obtain crystals. By the above procedure there was obtained 3-[(4-benzhydryl-1-homopiperazinyl)methyl]-7-morpholino-1,2-dihydronaphthalene hydrochloride melting at 173°–176° C.(decomposition).

Elemental analysis: Calculated for $C_{33}H_{39}N_3O.3HCl.CH_3COOC_2H_5.2H_2O$: C, 61.11; H, 7.07; N, 5.78. Found: C, 60.63; H, 7.00; N, 6.04.

EXAMPLE 9

For use as a drug for the treatment of essential hypertension, the present compound (1) may be administered, for example in the following dosage forms.

1. Tablets (1) 3-[(4-benzhydryl-1-piperazinyl)methyl]-7-piperidono-

| 1. Tablets | |
|---|---|
| 1,2-dihydronaphthalene hydrochloride | 10 mg. |
| (2) Lactose | 90 mg. |
| (3) Corn starch | 29 mg. |
| (4) Magnesium stearate | 1 mg. |
| | 130 mg. per tablet |

The ingredients (1) and (2) are mixed with 17 mg. of corn starch and the mixture is granulated with a paste prepared from 7 mg. of corn starch. To the granules are added the ingredient (4) and 5 mg. of starch and the entire mixture is compression-molded into a tablet 7 mm. in diameter.

| 2. Capsules | |
|---|---|
| (1) 3-[(4-Benzhydryl-1-piperazinyl)methyl]-7-morpholino-1,2-dihydronaphthalene hydrochloride | 10 mg. |
| (2) Lactose | 135 mg. |
| (3) Fine cellulose powder | 70 mg. |
| (4) Magnesium stearate | 5 mg. |
| | 220 mg. per capsule |

All the above ingredients are admixed and filled into a gelatin capsule No. 3 (The Pharmacopoeia of Japan, 8th Edition).

| 3. Injectable solution | |
|---|---|
| (1) 3-[(4-Benzhydryl-1-piperazinyl)methyl]-7-piperidine-1,2-dihydronaphthalene hydrochloride | 1 mg. |
| (2) Sodium chloride | 9 mg. |
| (3) Chlorobutanol | 5 mg. |
| (4) Sodium hydrogen carbonate | 1 mg. |

All the above ingredients are dissolved in 1 ml. of distilled water and filled into a brown-colored ampoule, followed by purging with nitrogen gas and sealing. The entire operation is aseptically carried out.

EXPERIMENT 1

The antihypertensive action of the representatives of the compounds (I):

[Testing procedure]

Male rats with spontaneous hypertension, weighing 240–310 g. and aged 9 to 15 weeks were used. Under non-anaesthesia, the systolic blood pressure of the tail artery was measured by plethysmography using an automatic blood pressure measuring apparatus. Three consecutive measurements were carried out and the average of results was taken as the blood pressure.

In evaluating the antihypertensive activity of each test compound, a suspension of the compound in 2% gum arabic and, as control, a 2% solution of gum arabic were respectively administered orally to rats in groups of 3 animals. The blood pressure measurements were carried out at hours 1, 3 and 5 after dosing and the effect of the test compound was evaluated in terms of the change in blood pressure from the level prior to dosing. Levels of significance were studied by the Student t-test with the blood pressure data for the control group as reference.

[Results]

The results of the above experiment are set forth in Table 1.

Table 1

| Test compound Structural formula | A | Dosage (mg./kg.) | Blood pressure before dosing (mmHg) | Change in blood pressure after dosing (mmHg) | | |
|---|---|---|---|---|---|---|
| | | | | 1 hour | 3 hours | 5 hours |
| 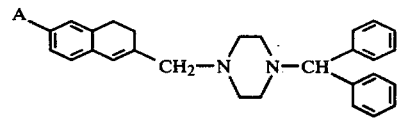 | 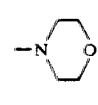 | 30 | 184 ± 10 | *<br>−84 ± 10 | *<br>−96 ± 9 | ***<br>−91 ± 11 |
| 3HCl | | | | | | |
| | 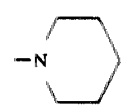 | 30 | 183 ± 11 | <br>−44 ± 5 | <br>−58 ± 6 | **<br>−62 ± 9 |
| | 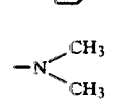 | 30 | 187 ± 3 | −12 ± 13 | *<br>−92 ± 17 | **<br>−60 ± 9 |
| | 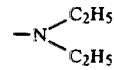  −N(CH₃)₂ | 30 | 189 ± 11 | <br>−72 ± 11 | <br>−74 ± 20 | **<br>−71 ± 5 |
| | −N(C₂H₅)₂ | 10 | 185 ± 10 | <br>−42 ± 7 | <br>−82 ± 11 | *<br>−57 ± 9 |

\* P<0.05;
\*\* P<0.01;
\*\*\* P<0.001

EXPERIMENT 2

The cerebral blood flow increasing action of the representatives of the compounds (I):

[Testing procedure]

Dogs weighing 5.5 to 12 kg. were anaesthetized with sodium pentobarbital (30 mg./kg., intravenous injection), and the increase in vertebral blood flow following the administration of the test compounds (intravenous injection) was determined, with an electromagnetic flowmeter set around the right vertebral artery.

[Results]

The results of the above experiment are set forth in Table 2.

Table 2

| Test compound Structural formula | A | n | Dosage (mg./Kg.) | No. of animals | Percent increase in blood flow in vertebral artery*[1] | | |
|---|---|---|---|---|---|---|---|
| | | | | | 5 minutes after dosing | 10 minutes after dosing | 30 minutes after dosing |
| 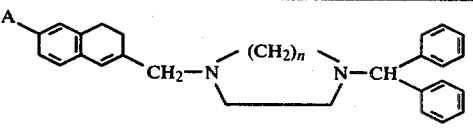<br>3HCl | −N(CH₃)₂ | 2 | 1.0 | 2 | 77 | 83 | 80 |
| | −N(C₂H₅)₂ | 2 | 0.1 | 2 | 21 | 31 | 31 |
| | 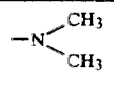 | 2 | 0.1 | 2 | 31 | 33 | 10 |
| | 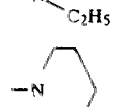 | 2 | 0.1 | 2 | 23 | 48 | 84 |
| | 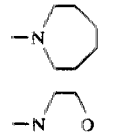 | 2 | 1.0 | 2 | 22 | 28 | 44 |

Table 2-continued

| Test compound | | | | | Percent increase in blood flow in vertebral artery[(1)] | | |
|---|---|---|---|---|---|---|---|
| Structural formula | A | n | Dosage (mg./Kg.) | No. of animals | 5 minutes after dosing | 10 minutes after dosing | 30 minutes after dosing |
| |  | 3 | 1.0 | 3 | 226 | 170 | 87 |

[(1)]Percent increase = $\dfrac{\text{Blood flow after dosing} - \text{Blood flow before dosing}}{\text{Blood flow before dosing}} \times 100$

What is claimed is:

1. A compound of the formula

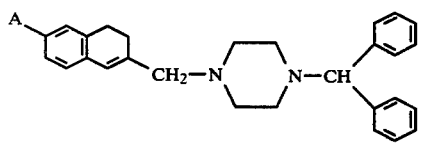

wherein A is 1-pyrrolidinyl, piperidino or 1-homopiperidinyl or an acid addition salt thereof.

2. A compound according to claim 1, wherein A is piperidino.

3. A compound according to claim 1, wherein the acid addition salt is hydrochloride.

4. A compound according to claim 1, said compound being 3-[(4-benzhydryl-1-piperazinyl)methyl]-7-piperidino-1,2-dihydronaphthalene.

5. A pharmaceutical composition which comprises, as the active ingredient, a vasodilator effective amount of at least one compound of the formula

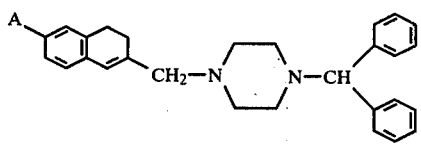

wherein A is 1-pyrrolidinyl, piperidino or 1-homopiperidinyl or an acid addition salt thereof together with a pharmaceutically acceptable carrier, excipient or diluent.